United States Patent [19]
Corcoran

[11] Patent Number: 5,752,524
[45] Date of Patent: May 19, 1998

[54] DEVICE FOR PREVENTING OR REDUCING SNORING

[76] Inventor: Timothy C. Corcoran, 3369 Fairway, Bay City, Mich. 48706

[21] Appl. No.: 873,486

[22] Filed: Jun. 12, 1997

[51] Int. Cl.$^6$ ........................................ A61F 5/56
[52] U.S. Cl. ................................. 128/848; 602/902
[58] Field of Search .................... 128/846, 848, 128/857–862; 2/2; 606/199, 204.35, 204.45; 602/902

[56] References Cited

U.S. PATENT DOCUMENTS

| | | | |
|---|---|---|---|
| Re. 35,408 | 12/1996 | Petruson | 128/858 |
| 1,292,083 | 1/1919 | Sawyer | 606/199 |
| 1,354,652 | 10/1920 | Jefferies . | |
| 1,850,540 | 3/1932 | Erickson . | |
| 3,594,813 | 7/1971 | Sanderson . | |
| 3,782,372 | 1/1974 | Carlton | 606/204.35 |
| 4,719,909 | 1/1988 | Micchia et al. . | |
| 4,817,636 | 4/1989 | Woods | 128/848 |
| 5,022,389 | 6/1991 | Brennan | 606/204.45 |
| 5,669,377 | 9/1997 | Fenn | 128/200.24 |

FOREIGN PATENT DOCUMENTS

| | | |
|---|---|---|
| 2420338 | 11/1979 | France . |
| 3837277 | 5/1990 | Germany . |

*Primary Examiner*—Michael A. Brown
*Attorney, Agent, or Firm*—Robert L. McKellar

[57] ABSTRACT

The device includes in combination a rigid ellipsoidal support base having a concave interior surface and a convex exterior surface and an adhesive material for attaching to human epidermis layered on a predominance of the entire convex interior surface. The device is particularly useful to prevent snoring in a sleeping human by providing support to the maxillofacial muscles of a user's face to provide a small air passage between the maxillofacial muscles of the face and the jaws which allows for the intake and output of air such that the sleeping individual does not have to intake and output air through the nose.

12 Claims, 1 Drawing Sheet

DEVICE FOR PREVENTING OR REDUCING SNORING

The invention disclosed and claimed herein deals with an anti-snoring device that is easily assembled and stored and is relatively inexpensive to manufacture. Further, the device of this invention can be a disposable item in that it can be used several times before disposing.

The device disclosed herein is particularly useful to prevent snoring in a sleeping human by providing a small air passage between the superior maxillary facial muscles of the face, and the superior maxilla (upper jaw bone), which allows for the intake and output of air such that the sleeping individual does not have to intake and output air through the nose. By this means, snoring is prevented, or markedly reduced.

BACKGROUND OF THE INVENTION

This invention deals with an anti-snoring device for the prevention or reduction of snoring in a sleeping human.

The device is designed for and is intended to be worn on the face of a human and the inventor herein is aware of a device that is designed and intended to be worn on the face. Such a device can be found in U.S. Pat. No. 1,850,540, which issued on Mar. 22, 1932 to Erickson. Such device is intended to be a protective shield and is further intended to be a flexible card or the like which is held in one hand over the part or member which needs protecting while a facial treating material is applied with the other hand, the edges of the card being curved in various ways so as to form parts that are applicable in various ways and which will conform to the shape or curvature of the body part being treated. This device is not intended to be actually worn, as much as it is intended to be applied and hand-held to the face. Thus, the device does not have an adhesive layer. In addition, as it will become evident infra, this device does not have a supporting function as does the device of the instant invention.

There are additional prior art devices for treating afflictions and which are intended to be used on or near the face. One such device can be found for instance in U.S. Pat. No. 1,354,652, issued to Jefferies on Oct. 5, 1920, in which there is shown a device to prevent mouth breathing, leading to a tendency to force breathing through the nose. The device allegedly assists in harmonizing the facial features of the wearer by more evenly balancing the muscles of expression.

Another such device can be found in U.S. Pat. No. 3,594,813, which issued to Sanderson, in which there is shown a protective device for protecting body portions which are exposed to large amounts of the radiation from the sun. The device is molded into the shape of the body portion from a material which is form-retaining, tear-resistant, soft, flexible and lightweight and an adhesive is provided on the inner surfaces of the device. Further, the device is ventilated through pores or by the manner in which the adhesive is distributed on the inner surf aces. In spite of the ability to adhere and conform to certain body parts, and in spite of the fact that the device has an inner adhesive, the device differs from the device of the instant invention in that it does not have a supporting function and does not provide the configuration necessary for the prevention of snoring. Further, the device is illustrated as a cover for the human nose.

In U.S. Pat. No. 4,719,909, there is shown an under-eye light absorbing device and a method of using.

In U.S. Pat. No. 4,817,636, which issued on Apr. 4, 1989, to Woods, there is shown an anti-snoring device comprising a sheet of flexible, tear-resistant material having a hypoallergenic adhesive applied to the back face of the material, and a protective backing sheet covering the adhesive back of said material, wherein the device is adapted to cover a user's mouth completely, has sides which converge towards the top to conform to the user's cheekline, and a top which has a central depression to conform to the user's nose and nostrils. Thus, the device is applied externally over the user's mouth to provide an anti-snoring device which conforms to the area bounded by a user's nose and cheekline such that it can be worn with minimal discomfort. This device is intended to close off the mouth and provide for breathing through the nose, quite the opposite effect intended by the instant invention. Further, this prior art device does not have a supporting function.

Further, there is shown an anti-snoring device in German DE 3837277 A1, in the name of Obermeier, J. having a date of Mar. 11, 1988, which is comprised of a strip with wide adhesive surfaces for placement on human lips and with a narrower weakened portion therebetween. The strip is intended to cover and seal the lips of the wearer together to prevent breathing through the mouth. The strip has a weakened narrow portion which is tearable if the user has a sneeze or the like. The device has the same disadvantages as the prior art device just above. It has the opposite intended use in that it covers the mouth, and it does not have any supporting function.

Finally, there is shown in French Patent 78 08083, in the name of Josef Blander, an anti-snoring mask which is an elliptical sheet of a film made from cellophane or polyethylene intended to cover the orbicular muscles of the human lips with the mouth wide open. The sheet is pressed in order to adapt itself to the shape of the lips and the device has an edging of adhesive in order to hermetically adhere the device to the tissue surrounding the lips, but not bind the lips. With the device, it is intended that the user not be able to breath orally, and thus cause the user to automatically breath through the nose. This device is just a mask and does not have a supporting function and further, its configuration is such that it has to be worn over the lips and cover the mouth, which is the opposite function intended for the device of the instant invention.

None of the devices of the prior art described above provide the benefits of the device of the instant invention.

THE INVENTION

The invention herein deals with an anti-snoring device that is easily manufactured, is inexpensive to manufacture, and is markedly useful for preventing snoring in humans while sleeping.

Such a device is therefore an anti-snoring device comprising in combination a rigid support base having a concave interior surface and a convex exterior surface, and an adhesive material for attaching to human epidermis layered on a predominance of the entire convex interior surface.

The invention herein also contemplates a method of reducing snoring in a human, the method comprising applying one or more of the devices described just above, to a human face covering at least a portion of the superior maxillary facial muscles of said human face, applying pressure to the facial muscles and the device simultaneously to adhere the device to the superior maxillary facial muscles, and, allowing each of the devices to remain in place while the human sleeps.

DETAILED DESCRIPTION OF THE INVENTION

As can be observed from the discussion of the prior art supra, there are several devices intended to prevent snoring in humans. Such devices either require the use of devices that are placed in the mouth, or in the nose, or require the use of straps tied around the head or neck, or provide for a covering over the mouth to force breathing through the nose.

Such devices are awkward, maybe dangerous, and seem to have a quite different theory on how to prevent snoring.

It is therefore an object of the present invention to provide an anti-snoring device which is applied to the superior maxillary facial muscles of the face to support the underlaying muscles such that the muscles are not touching the internal parts of the mouth, essentially the superior maxillary. Such a supported device thus provides for a small air passage to be created so that normal breathing can be had through the mouth, rather than the nose, which normal breathing prevents forced breathing through the nose, and thus prevents snoring.

A further object of the present invention is to provide a process for preventing snoring in humans.

The objects are met by the invention which comprises an anti-snoring device that is easily manufactured, is inexpensive to manufacture, and is markedly useful for preventing snoring in humans while sleeping.

Such a device is therefore an anti-snoring device comprising in combination a rigid support base having a concave interior surface and a convex exterior surface, and an adhesive material for attaching to human epidermis layered on a predominance of the entire convex interior surface.

Figure 1:
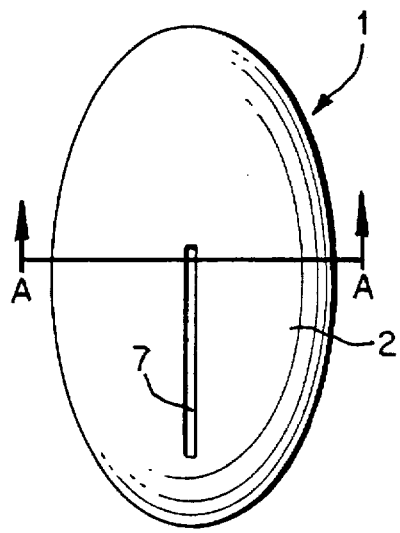
FIG. 1 is a full top view of a device of this invention.
Figure 2:
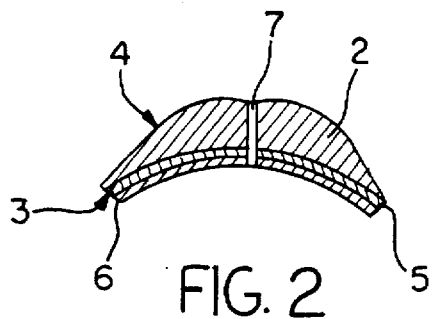
FIG. 2 is a cross-sectional view of the device of FIG. 1, at about the midpoint of the device as shown by line A—A.
Figure 3:
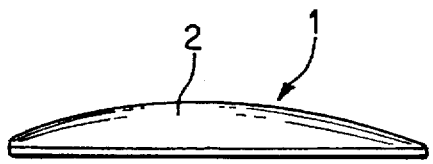
FIG. 3 is a full side view of the device of FIG. 1.

Now, with reference to FIGS. 1, 2, and 3, and with especial reference to FIG. 1, there is shown a full top view of a device 1 of this invention, in which there is shown a rigid ellipsoidal cupped base 2. The rigidity of the base should be such that the device, when applied as will be discussed infra, actually supports the muscles underlaying it. For example, the base 2 can be manufactured from rigid plastics, flexible plastics that have the capability of providing the intended muscle support, lightweight metals, cardboard, or multiple layered paper, rubber, glass, and the like. Preferred are rigid plastics such as thermoset plastics and lightweight metals such as aluminum. Thus, when the device is applied to the muscles of the face and attached as described infra, the base must have the ability to slightly lift the muscles of the face from the underlaying bone and tissue structure to create an air passage. Any material that has sufficient rigidity to accomplish this support is useful in this invention.

The base 2 is shown as an ellipsoidal cup because of the fact that some length is preferred in the base in order to lift sufficient facial muscle to provide an adequate air passage. It is contemplated within the scope of this invention to use shorter ellipsoidal cups, that approach a round configuration in order to accomplish essentially the same support. Further, it is contemplated within the scope of this invention to use rounded cups.

The base 2 has a concave interior surface 3 and a convex exterior surface 4 as is shown in FIG. 2.

There is also shown in FIG. 2, an adhesive layer 5, attached directly to the concave interior surface 3. The adhesive layer 5 for purposes of this invention should be evenly layered over the predominance of the concave interior surface 3, but it is contemplated within the scope of this invention to provide devices 1 having less of the surface area covered by the adhesive layer 5. For purposes of this invention, the determining factor is whether or not there is sufficient adhesive of the adhesive layer 5 to hold the device 1 to the facial muscles of the face for the duration of the sleep period of the human. Thus, this time can be anyperiod of time from a few minutes to several hours. The adhesive of the adhesive layer 5 can be any adhesive that will sufficiently adhere to the human skin for the time periods set forth just above. However, preferred is an adhesive that is a sterile, pressure-sensitive adhesive, and most preferred is a sterile, pressure-sensitive, hypoallergenic adhesive.

The adhesive is preferably a non-drying, tacky adhesive that can be readily removed from the skin without injuring the skin.

Layered over the adhesive layer 5 is a backing sheet 6. Preferably, the backing sheet 6 is a strippable protective cover and is made of paper, or thin films of plastic that can be layered on the adhesive layer 5, and which attaches to the adhesive layer 5, but can be readily removed with a small force. The backing sheet 6 should be large enough to cover essentially all of the adhesive layer 5 so that the device does not contact and attach to other, unwanted surfaces. Further, the backing sheet 6 should be large enough in some cases to cover the entire adhesive layer 5 surface such that the sterile integrity of the adhesive layer 5 is maintained during storage, such configuration including covering the edges of the adhesive layer.

Figure 4:
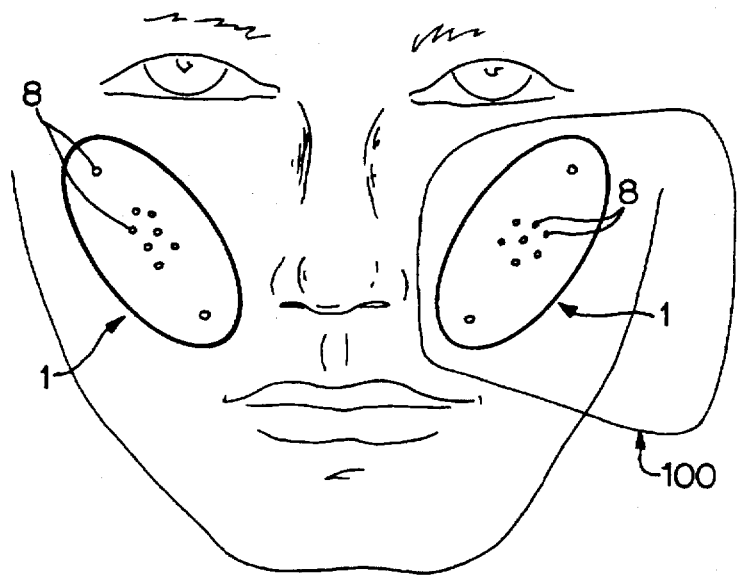
FIG. 4 is a partial front view of a user's face showing the devices of this invention in place on the superior maxillary facial muscles of the face.

There is shown in FIGS. 1 and 2, an air slot 7 for passage of air from the skin underneath the device 1 to the outside, in order to provide breathing for the underlaying skin. Although shown as a slot 7, the same effect can be provided by small holes or some such similar means, as long as the underlaying skin has an opportunity to breath. Thus, contemplated within the scope of this invention is a device 1 as is shown in FIG. 4 wherein there are multiple holes 8 to provide this transportation of perspiration. This breathing is essentially required to allow perspiration to move from underneath the device 1 to the outside and keep the underlaying skin cool.

Figure 5:
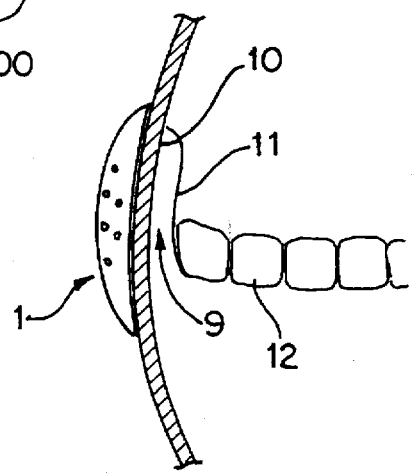
FIG. 5 is a partial view of the face of FIG. 4, in the area designated 100 and wherein the superior maxillary facial muscle is shown in cross-section.

FIG. 5 is a partial segment designated at 100 in FIG. 4, in which there is shown a front view of a part of the face, showing the placement of the device 1, and the air passage 9 provided therein. It should be understood that when a person is in the prone position for sleeping, the superior maxillary facial muscles 10, shown in cross-section in FIG. 5, collapse onto the underlaying bone and tissue structure, shown herein as the gum line 11 and the teeth 12, thus creating a condition wherein the air passages from the mouth to the throat are very narrowly constricted. Any small change in the configuration of the muscles 10, that opens the general space 9 within the mouth, tends to provide an adequate air passage leading to the reduction, or elimination of snoring to provide normal breathing.

In some persons, whose superior maxillary facial muscles tend to be full and rounded, this condition is most egregious, and the device of this invention when used as indicated infra, markedly eliminates, or in some cases, reduces snoring.

The invention herein also contemplates a method of reducing snoring in a human, the method comprising applying one or more of the devices described just above to a human face covering at least a portion of the superior maxillary facial muscles of said human face, applying pressure to the superior maxillary facial muscles and the device simultaneously to adhere the device to the superior maxillary facial muscles, and, allowing each of the devices to remain in place while the human sleeps.

Typically, this can be accomplished by stripping the backing sheet 6 from the adhesive layer 5, placing the device 1 against the cheek at the region of the superior maxillary facial muscle, and while holding the device 1 in place, applying pressure from within the mouth, either by using the tongue, or fingers. As the skin contacts the adhesive layer 5, the adhesion is instantaneous. The device 1 will then stay in place as long as the user wishes it to.

When removing, the device 1 is simply peeled from the skin. Typically, the backing sheet 6 can be replaced on the adhesive to preserve the device 1 for further use. Eventually, through repeated use, the adhesive loses its tackiness and the device 1 can be discarded.

It has been found by the inventor herein that such devices are comfortable to wear, do not disturb the user's sleep, and are relative inexpensive to make and use. This use leads to more sound and restful sleep and contributes to the user's overall general health.

What is claimed is:

1. An anti-snoring device comprising in combination:
   (i) a rigid support base having a concave interior surface and a convex exterior surface, and,
   (ii) an adhesive material for attaching to human epidermis, layered on a predominance of the entire concave interior surface.

2. An anti-snoring device as claimed in claim 1 wherein, in addition, the adhesive is covered with a strippable protective cover.

3. An anti-snoring device as claimed in claim 1 wherein there is also present an opening, said opening projecting from the convex exterior surface through the adhesive to create an air passage from the epidermis to the convex exterior surface of the anti-snoring device.

4. The device as claimed in claim 1 wherein the base is manufactured from plastic.

5. The device as claimed in claim 1 wherein the base is manufactured from metal.

6. The device as claimed in claim 1 wherein the base is manufactured from paper.

7. The device as claimed in claim 1 wherein the base is manufactured from cardboard.

8. The device as claimed in claim 1 wherein the base is manufactured from rubber.

9. The device as claimed in claim 1 wherein the base is manufactured from glass.

10. The device as claimed in claim 1 which is configured as an ellipsoidal cup.

11. The device as claimed in claim 1 which is configured as a round cup.

12. A method of reducing snoring in a human, the method comprising:
   (a) applying one or more of the devices of claim 1 to a human face covering at least a portion of epidermis over the superior maxillary facial muscles of said human face;
   (b) applying pressure to the superior maxillary facial muscles and the device to adhere the device to the epidermis over the superior maxillary facial muscles, and,
   (c) allowing each of the devices to remain in place while the human sleeps.

* * * * *